US006368607B1

(12) United States Patent
Rerek et al.

(10) Patent No.: US 6,368,607 B1
(45) Date of Patent: *Apr. 9, 2002

(54) PRODUCT-STRUCTURANT COMPOSITION FOR PERSONAL CARE FORMULATIONS

(75) Inventors: Mark Rerek, Scotch Plains; Chester Wang, Livingston, both of NJ (US); Elliott Zucker, Shohola, PA (US); David Moore, Upper Montclair; Ilya Makarovskiy, North Arlington, both of NJ (US)

(73) Assignee: ISP Investments Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/395,382

(22) Filed: Sep. 14, 1999

Related U.S. Application Data

(63) Continuation-in-part of application No. 09/122,152, filed on Jul. 24, 1998, now abandoned.

(51) Int. Cl.$^7$ ............... A61K 7/00; A61K 7/075; A61K 7/06; A61K 7/48

(52) U.S. Cl. ............ 424/401; 424/450; 424/59; 424/70.1; 424/70.28; 514/844; 514/847; 514/937; 514/943

(58) Field of Search ................. 424/401, 450, 424/59, 70.1, 70.28; 514/844–848, 880, 881, 938

(56) References Cited

U.S. PATENT DOCUMENTS

| | | | | |
|---|---|---|---|---|
| 4,012,398 A | * | 3/1977 | Conner | 260/404.5 |
| 5,510,120 A | * | 4/1996 | Jones | 424/499 |
| 5,560,918 A | * | 10/1996 | Wivell | 424/401 |

* cited by examiner

*Primary Examiner*—Gollamudi S. Kishore
(74) *Attorney, Agent, or Firm*—Walter Katz; William J. Davis; Marilyn J. Maue

(57) ABSTRACT

A product-structuring composition which forms a bilayer lamellar gel network in an oil-in-water system comprising (a) a cationic swellant which is a fatty acid adduct of amidopropyldimethyl-2-hydroxyethyl ammonium halide, and (b) a gellant blend of low HLB emulsifiers having a resultant HLB of about 1.5 to 4.5.

14 Claims, No Drawings

PRODUCT-STRUCTURANT COMPOSITION FOR PERSONAL CARE FORMULATIONS

CROSS REFERENCE TO RELATED U.S. PATENT APPLICATION

This is a continuation-in-part application based upon U.S. Ser. No. 09/122,152, filed Jul. 24, 1998 now abandoned.

BACKGROUND OF THE INVENTION

1. Field of the Invention

This invention relates to compositions for personal care formulations, and, more particularly, to a cationic product-structurant composition which forms a bilayer lamellar gel network in an oil-in-water system, thereby to provide a skin feel of lubricity and emollience, skin conditioning, and skin barrier strengthening which brings moisturization to the user without added moisturizer, sun protection through uniform delivery of active sunscreens, and provision of a uniform color from a liquid make-up formulation, as well as effective hair conditioning.

2. Description of the Prior Art

Human body skin forms a barrier which protects the body against uncontrolled loss of water. The outermost layer of the skin, the stratum corneum, provides this barrier. Traditionally, the stratum corneum has been described as a bricks-and-mortar structure in which the corneocyte "bricks" are surrounded by lipid "mortar". The lipid region is known to provide the semi-permeability barrier needed for healthy skin, and the physical organization of the lipids is known to be critical for good barrier function.

Skin lipids have been the subject of much research in recent years, and the relatively simple "mortar" model has recently evolved into a more complex "Domain Mosaic Model" (DMM). In this model, skin lipids are described as having domains of solid or gel-state lipids bordered by lipids in a more fluid liquid crystalline state called a "grain boundary".

A DMM arrangement provides an effective barrier that prevents the indiscriminate loss of water, yet allows controlled evaporation to regulate body temperature. The more fluid character of the grain boundaries represents areas where materials may diffuse in or out of the system. However, any loss of lipid can disrupt the barrier function of the stratum corneum. Healthy skin thus requires optimal barrier function and maintenance of skin moisture for prevention of irritation and dryness.

Lipid loss can arise due to excess washing, exposure to cold and dry climates, or dietary unbalance. Lipid depletion eventually causes a weakened, more permeable barrier which readily loses moisture, resulting in rough, dry skin. A permeable barrier also is more readily penetrated by foreign materials which can cause effect adverse reactions in sensitive skin.

Lipids may be replenished by topical application of a skin care formulation. However, it is crucial that such lipids be present therein in suitable form if barrier function is to be rapidly restored, preferably in a bilayer lamellar gel network which approximate the structure of lipids within the stratum corneum. Such bilayer lamellar gel networks also can provide product-structuring of oil-in-water emulsions by formation of multilayer vesicles with the oil phase and extended bilayer sheets throughout the water phase which eliminates the need for application of conventional emulsifiers that do not provide any benefit to the skin.

Conner et al in U.S. Pat. No. 4,012,398, described an emollient composition having hair conditioning properties which was the reaction product of mink oil, dimethylaminopropylamine and enchlorohydrin. However, the unsaturated fatty acids present in mink oil have been found to be unsatisfactory for lamellar gel networks.

Accordingly, it is an object of this invention to provide a cationic skin conditioning agent, and product-structuring or emulsion compositions therewith, in the form of a cationic bilayer lamellar gel network which approximates the natural structure of the stratum corneum lipids and is stable to temperatures up to 80° C., wherein the cationic (negative charged) lamellar gel is strongly attracted to human skin, so that the charge interaction between the skin and the lamellar gel provides excellent skin coverage, effective skin conditioning, and long-lasting barrier enhancement.

Yet another object herein is to provide skin care formulations including such cationic bilayer lamellar gel network compositions and resulting emulsion formulations, having a skin feel of lubricity and emollience, and which provides moisturization without added moisturizer, and which can deliver active sunscreens to the skin surface by the cationic bilayer lamellar gel network system thus providing excellent, long-lasting photoprotection.

A particular object herein is to provide product-structuring or emulsion compositions and skin care formulations therewith whose skin feel is moist and substantive in their skin feel after use.

These and other objects and features of the invention will be made apparent from the following description.

SUMMARY OF THE INVENTION

What is described herein is a product-structuring composition which will form a bilayer lamellar gel network in an oil-in-water system comprising (a) a cationic swellant which is a fatty acid adduct of amidopropyldimethyl-2-hydroxyethyl ammonium halide, and (b) a gellant blend of low HLB emulsifiers having a resultant HLB of about 1.5 to 4.5.

Preferably the composition includes a saturated fatty acid such as stearic or palmitic acid, or mixtures thereof, suitably present in an amount, by weight, of about 0.5 to 5% of the composition and (b) being the remainder 100%.

Preferably (b) includes a group of emulsifiers having a non-ionizable group selected from fatty alcohols and esters, optionally with an ionizable emulsifier which is a fatty acid, particularly wherein said fatty alcohol is behenyl alcohol and said fatty ester is glycerol stearate or sorbitan monostearate, or mixtures thereof, in a weight ratio of fatty ester to fatty alcohol of about 2:1 to about 1.6:1, and the weight ratio of saturated fatty acid emulsifier to (a) is about 2:1 to about 4:1.

A preferred composition is wherein (b) comprises by weight, about 30–60% glycerol stearate, about 25–50% cetyl alcohol, about 3–8% behenyl alcohol and about 2–8% of a mixture of palmitic and stearic acids.

Also described herein are personal care formulations having about 2–8% of the product-structuring composition, such as skin care, hair conditioning and sunscreen formulations.

BRIEF DESCRIPTION OF THE INVENTION

The swellant in the product-structuring composition of the invention is the reaction product of a fatty acid, preferably a saturated fatty acid, e.g. palmitic/stearic acid, and dimethyl aminopropyl amine and epichlorohydrin, which is a cationic quaternary compound, e.g. palmityl/stearyl amidopropyl dimethyl 2-hydroxyethyl ammonium chloride. Generally, the reaction is run in a suitable non-volatile solvent, preferably an oil soluble solvent, at a suitable temperature. Preferred solvents for use herein are fatty alcohols which are oil soluble, such as stearyl alcohol, behenyl alcohol and cetyl alcohol.

The bilayer lamellar gel network product-structuring composition of the invention is a mixture of such cationic quaternary conditioning agent, i.e. the saturated fatty acid adduct of amidopropyl dimethyl 2-hydroxyethyl ammonium chloride, in a weight amount of about 0.5 to 5%, preferably about 0.75 to 3%, and, optimally about 1 to 2%, and a blend of low HLB emulsifiers, to 100%. The blend of low HLB emulsifiers has a resultant HLB of about 1.5 to 4.5, preferably about 2 to 4, and, optimally about 2.7 to 3.2.

The low HLB blend is selected from a group of emulsifiers having a non-ionizable group, e.g. fatty alcohols such as behenyl alcohol (HLB=1.9), and esters such as glycerol stearate (HLB=3.4) and sorbitan monostearate (HLB=4.7). In a preferred form of the invention, the weight ratio of ester to fatty alcohol is about 2:1 to about 1.6 to 1. Additionally, an ionizable emulsifier such as a fatty acid may be added to provide compatibility with anionic thickeners. Preferably, the weight ratio of the fatty acid, e.g. stearic/palmitic acid, to the cationic quaternary conditioning agent is about 2:1 to about 4 to 1.

A personal care formulation is made by including about 2–8% by weight, preferably 3–6%, of the product-structurant composition in the formulation. In one embodiment, the gellant in such composition comprises about 30–60% glycerol stearate, about 25–50% cetearyl alcohol, about 3–8% behenyl alcohol, and about 2–8% of a mixture of palmitic and stearic acids.

The gel network formed by the product-structuring composition of the invention begins a phase transition above 45° C. in most emulsion products. Therefore, to ensure high temperature stability for the skin care formulation, it is preferred to add a small amount of a hydrocolloid thickener such as Stabileze QM® (International Specialty Products), which is a crosslinked methyl vinyl ether/maleic anhydride copolymer.

The skin care formulations, and product-structuring composition therefor, provides the user with a skin feel of lubricity and emollience, as well as moisturization without added moisturizer.

The term "fatty" acids and alcohols, as used herein, refers to compounds having from 12–26 carbon atoms.

The invention will now be described in more detail with reference to the following examples.

The following cationic bilayer lamellar gel network product-structurant compositions of Examples 1–5 were prepared by melting the components, mixing thoroughly, and cooling to room temperature.

Product-Structuring Compositions

EXAMPLE 1

| Swellant | Wt. % | Gellant | Wt. % | HLB |
|---|---|---|---|---|
| SAQ* | 2.0 | Glycerol stearate | 60.0 | 3.4 |
| | | Cetyl alcohol | 16.55 | 2.5 |
| | | Stearyl alcohol | 16.55 | 2.3 |
| | | Behenyl alcohol | 4.90 | 1.9 |
| | | Total | 98.0 | 2.93 |

EXAMPLE 2

| Swellant | Wt. % | Gellant | Wt. % | HLB |
|---|---|---|---|---|
| SAQ | 1.5 | Glycerol stearate | 61.0 | 3.4 |
| | | Cetyl alcohol | 16.51 | 2.5 |
| | | Stearyl alcohol | 16.51 | 2.3 |
| | | Palmitic acid | 2.48 | 3.3 |
| | | Stearic acid | 2.20 | 3.2 |
| | | Total | 98.5 | 3.01 |

*stearyl acid adduct of amidopropyl dimethyl 2-hydroxyethyl ammonium chloride

EXAMPLE 3

| Swellant | Wt. % | Gellant | Wt. % | HLB |
|---|---|---|---|---|
| SAQ | 1.0 | Glycerol stearate | 61.7 | 3.4 |
| | | Cetyl alcohol | 15.43 | 2.5 |
| | | Stearyl alcohol | 15.42 | 2.3 |
| | | Behenyl alcohol | 2.45 | 1.9 |
| | | Palmitic acid | 2.2 | 2.3 |
| | | Stearic acid | 1.8 | 2.2 |
| | | Total | 99.0 | 3.02 |

EXAMPLE 4

| Swellant | Wt. % | Gellant | Wt. % | HLB |
|---|---|---|---|---|
| SAQ | 1.0 | Glycerol stearate | 61.7 | 3.4 |
| | | Cetyl alcohol | 15.43 | 2.5 |
| | | Stearyl alcohol | 15.42 | 2.3 |
| | | Behenyl alcohol | 2.45 | 1.9 |
| | | Ricinoleyl monomaleate Triglyceride | 4.0 | 1.6 |
| | | Total | 99.0 | 2.95 |

EXAMPLE 5

| Swellant | Wt. % | Gellant | Wt. % | HLB |
|---|---|---|---|---|
| SAQ | 2.0 | Glycerol stearate | 60.0 | 3.4 |
| | | Behenyl alcohol | 38.0 | 1.9 |
| | | Total | 98.0 | 2.76 |

EXAMPLE 6

Into a four-neck, round-bottom glass flask, equipped with a Dean-Stark receiver, a water cooled condenser, a nitrogen purge, an overhead mechanical agitator and a temperature controller, was charged 76.8 g of palmitic acid and 38.3 g of 3-dimethylaminopropyl-amine (DMAPA). The resulting mixture was agitated at 160° C. for 4 hours, during which water of the ensuing amidation reaction was intermittently removed. After completion of amidation, excess DMAPA was removed by vacuum. The batch was cooled down to room temperature, 252.2 g of cetearyl alcohol was charged, along with 24.1 g of 2-chloroethanol. The resulting mixture was agitated at 140° C. for 4 hours. Upon completion, the product was flaked at 110° C. to give a pale yellow material as palmitic amidopropyl dimethyl 2-hydroxyethyl ammonium chloride and cetearyl alcohol.

EXAMPLE 7

Example 6 was repeated except that 252.2 g of behenyl alcohol was substituted for cetearyl alcohol. The corresponding product, palmitic amidopropyl dimethyl 2-hydroxy-ethyl ammonium chloride and cetearyl alcohol were recovered as pale yellow flakes.

EXAMPLE 8

Example 6 was repeated except that 37.5 g of 2-bromoethanol was substituted for 2-chloroethanol. The corresponding product, palmitic amidopropyl dimethyl 2-hydroxy-ethyl ammonium bromide and cetearyl alcohol were recovered as pale yellow flakes.

EXAMPLE 9

Example 6 was repeated except that 51.6 g of 2-iodoethanol was substituted for 2-chloro-ethanol. The corresponding product, palmitic amidopropyl dimethyl 2-hydroxyethyl ammonium iodide and cetearyl alcohol were recovered as pale yellow flakes.

EXAMPLE 10

Example 6 was repeated except that 15.5 g of 2-fluoroethanol was substituted for 2-chloroethanol. The corresponding product, palmitic amidopropyl dimethyl 2-hydroxy-ethyl ammonium fluoride and cetearyl alcohol were recovered as pale yellow flakes.

EXAMPLE 11

Example 6 was repeated except that 85.2 g stearic acid was substituted for palmitic acid. The corresponding product, stearic amidopropyl dimethyl 2-hydroxyethyl ammonium chloride and cetearyl alcohol were recovered as pale yellow flakes.

EXAMPLE 12

Example 11 was repeated except that 252.2 g behenyl alcohol was substituted for cetearyl alcohol. The corresponding product, stearic amidopropyl dimethyl 2-hydroxyethyl ammonium chloride and behenyl alcohol were recovered as pale yellow flakes.

EXAMPLE 13

Example 11 was repeated except that 37.5 g of 2-bromoethanol was substituted for 2-chloroethanol. The corresponding product, stearic amidopropyl dimethyl 2-hydroxyethyl ammonium bromide and cetearyl alcohol were recovered as pale yellow flakes.

EXAMPLE 14

Example 11 was repeated except that 51.6 g of 2-iodoethanol was substituted for 2-chloro-ethanol. The corresponding product, stearic amidopropyl dimethyl 2-hydroxyethyl ammonium iodide and cetearyl alcohol were recovered as pale yellow flakes.

EXAMPLE 15

Using the equipment of Example 1, 89.3 g of ricebran oil, 10.2 g of DMAPA and 0.2 g sodium hydroxide were charged. The resulting mixture was agitated at 140° C. for 4 hours. After completion of amidation, excess DMAPA was removed by vacuum. The batch was cooled down to room temperature, 247.2 g of cetearyl alcohol was charged, along with 24.1 g of 2-chloroethanol. The resulting mixture was agitated at 140° C. for 4 hours. Upon completion, the product is flaked at 80° C. to give a yellow material as ricebran amidopropyl dimethyl 2-hydroxyethyl ammonium chloride and cetearyl alcohol.

EXAMPLE 16

Example 15 was repeated except that 37.5 g 2-bromoethanol was substituted for 2-chloroethanol. The corresponding product, ricebran amidopropyl dimethyl 2-hydroxy-ethyl ammonium bromide and cetearyl alcohol were recovered as yellow flakes.

EXAMPLE 17

Example 15 was repeated except that 247.2 g behenyl alcohol was substituted for cetearyl alcohol. The corresponding product, ricebran amidopropyl dimethyl 2-hydroxyethyl ammonium chloride and behenyl alcohol were recovered as pale yellow flakes.

EXAMPLE 18

Example 15 was repeated except that 88.1 g safflower oil was substituted for ricebran oil. The corresponding product, safflower amidopropyl dimethyl 2-hydroxyethyl ammonium chloride and cetearyl alcohol were recovered as yellow flakes.

EXAMPLE 19

Example 18 was repeated except that 247.2 g behenyl alcohol was substituted for cetearyl alcohol. The corresponding product, safflower amidopropyl dimethyl 2-hydroxyethyl ammonium chloride and behenyl alcohol were recovered as yellow flakes.

EXAMPLE 20

Example 18 was repeated except that 37.5 g 2-bromoethanol was substituted for 2-chloroethanol. The corresponding product, safflower amidopropyl dimethyl 2-hydroxy-ethyl ammonium bromide and cetearyl alcohol were recovered as yellow flakes.

EXAMPLE 21

Example 15 was repeated except that 87.7 g soybean oil was substituted for ricebran oil. The corresponding product, soybean amidopropyl dimethyl 2-hydroxyethyl ammonium chloride and cetearyl alcohol were recovered as yellow flakes.

EXAMPLE 22

Example 21 was repeated except that 247.2 g behenyl alcohol was substituted for cetearyl alcohol. The corresponding product, soybean amidopropyl dimethyl 2-hydroxy-ethyl ammonium chloride and behenyl alcohol were recovered as yellow flakes.

EXAMPLE 23

Example 21 was repeated except that 37.5 g 2-bromoethanol was substituted for 2-chloroethanol. The corresponding product, soybean amidopropyl dimethyl 2-hydroxy-ethyl ammonium bromide and cetearyl alcohol were recovered as yellow flakes.

EXAMPLE 24

Example 15 was repeated except that 84.2 g palm oil was substituted for ricebran oil. The corresponding product, palm amidopropyl dimethyl 2-hydroxyethyl ammonium chloride and cetearyl alcohol were recovered as yellow flakes.

EXAMPLE 25

Example 24 was repeated except that 247.2 g behenyl alcohol was substituted for cetearyl alcohol. The corresponding product, palm amidopropyl dimethyl 2-hydroxyethyl ammonium chloride and behenyl alcohol were recovered as yellow flakes.

EXAMPLE 26

Example 24 was repeated except that 37.5 g 2-bromoethanol was substituted for 2-chloroethanol. The corresponding product, palm amidopropyl dimethyl 2-hydroxy-ethyl ammonium bromide and cetearyl alcohol were recovered as yellow flakes.

The following examples 27–30 describes personal care formulations which include the product-structuring compositions of Examples 1–5.

EXAMPLE 27

SKIN MOISTURIZER CREAM

| Phase | Ingredient | A | B |
|---|---|---|---|
| A | Water | 67.6 | 68.6 |
|   | EDTA | 0.1 | 0.1 |
|   | Glycerin | 1.0 | 1.0 |
|   | Carbopol 940 (BF Goodrich) | 0.2 | — |
|   | Stabileze QM (ISP) | — | 0.2 |
| B | Ceraphyl 230 (ISP) | 4.0 | 4.0 |
|   | Ceraphyl 494 (ISP) | 6.0 | 6.0 |
|   | Ceraphyl 368 (ISP) | 10.0 | 10.0 |
|   | Composition of Example 3 | 5.0 | 4.0 |
| C | Water | 5.0 | 5.0 |
|   | NaOH (10% solution) | 0.5 | 0.5 |
| D | Liquid Germall Plus (ISP) | 0.6 | 0.6 |
|   | Total | 100 | 100 |

Procedure

Combine water, EDTA, and glycerin of phase A. Slowly sprinkle either Carbopol 940 or Stabileze QM into phase A with stirring at room temperature. Heat phase A to 70–75° C. Separately, combine phase B, then heat to 75–80° C. When both phase A and phase B are at temperature, add phase B to phase A with homogenization until batch appears uniform. Continue homogenization for 2 minutes while adding phase C. Switch to sweep agitation and remove heat. Add phase D at 35–40 C. Make up for lost water and stir until room temperature.

Skin care formulations A and B provide the user with a skin feel of lubricity and emollience, and provide moisturization without added moisturizer.

EXAMPLE 28

SKIN MOISTURIZER CREAM

| Phase | Ingredient | C | D | E |
|---|---|---|---|---|
| A | Water | 72.8 | 72.3 | 74.8 |
|   | EDTA | 0.1 | 0.1 | 0.1 |
|   | Glycerin | 1.0 | 1.0 | 1.0 |
|   | Guar Gum (TIC Gums Inc.) | 0.5 | — | — |
|   | Jaguar C-13S (Rhodia) | — | 1.0 | — |
|   | Keltrol T (Monsanto) | — | — | 0.5 |
| B | Ceraphyl 230 (ISP) | 4.0 | 4.0 | 4.0 |
|   | Ceraphyl 494 (ISP) | 6.0 | 6.0 | 6.0 |
|   | Ceraphyl 368 (ISP) | 10.0 | 10.0 | 10.0 |
|   | Composition of Example 3 | 5.0 | 5.0 | 3.0 |
| C | Liquid Germall Plus (ISP) | 0.6 | 0.6 | 0.6 |
|   | Total | 100 | 100 | 100 |

Procedure

Combine water and EDTA of phase A. Wet gum with glycerin. Slowly add glycerin mixture to phase A with stirring at room temperature. Heat phase A to 70–75° C. Separately, combine phase B, then heat to 75–80° C. When both phase A and phase B are at temperature, add phase B to phase A with homogenization until batch appears uniform. Continue homogenization and remove heat. Switch to sweep stirring at 40° C. Add phase C at 35–40° C. Make up for lost water and stir until room temperature.

Skin care formulations C, D and E provide the user with a skin feel of lubricity and emollience, and provide moisturization without added moisturizer.

EXAMPLE 29

SKIN MOISTURIZER CREAM

| Phase | Ingredient | F | G |
|---|---|---|---|
| A | Water | 71.8 | 71.8 |
|   | EDTA | 0.1 | 0.1 |
|   | Glycerin | 1.0 | 1.0 |
|   | Guar Gum (TIC Gums Inc.) | 0.5 | — |
|   | Locust Bean Gum (TIC Gums Inc.) | — | 0.5 |
| B | Ceraphyl 230 (ISP) | 4.0 | 4.0 |
|   | Ceraphyl 494 (ISP) | 6.0 | 6.0 |
|   | Ceraphyl 368 (ISP) | 10.0 | 10.0 |
|   | Composition of Example 5 | 5.0 | 5.0 |
| C | Ceraphyl 60 (ISP) | 1.0 | 1.0 |
| D | Liquid Germall Plus (ISP) | 0.6 | 0.6 |
|   | Total | 100 | 100 |

Procedure

Combine water and EDTA of phase A. Wet gum with glycerin. Slowly add glycerin mixture to phase A with stirring at room temperature. Heat phase A to 70–75° C. Separately, combine phase B then heat to 75–80° C. When both phase A and phase B are at temperature, add phase B to phase A with homogenization until batch appears uniform. Continue homogenization and remove heat. Switch to sweep stirring at 50° C. Add phase C at 45° C. Add phase D at 35–40° C. Make up for lost water and stir until room temperature.

Skin care formulations F and G provide the user with a skin feel of moistness, lubricity and emollience, and provide superior moisturization.

EXAMPLE 30

SUNSCREEN FORMULATION

| Phase | Ingredient | H |
|---|---|---|
| A | Water | 69.1 |
|   | EDTA | 0.1 |
|   | Glycerin | 1.0 |
|   | Carbopol 940 (BF Goodrich) | 0.2 |
| B | Escalol 557 (ISP) | 7.5 |
|   | Escalol 567 (ISP) | 3.0 |
|   | Escalol 587 (ISP) | 3.0 |
|   | Ceraphyl 368 (ISP) | 6.0 |
|   | Composition of Example 3 | 3.0 |
|   | Ganex V-220 (ISP) | 1.0 |
| C | Water | 5.0 |
|   | NaOH (10% solution) | 0.5 |
| D | Liquid Germall Plus (ISP) | 0.6 |
|   | Total | 100 |

Procedure

Combine water, EDTA, and glycerin of phase A. Slowly sprinkle either Carbopol 940 into phase A with stirring at room temperature. Heat phase A to 70–75° C. Separately, combine phase B, then heat to 75–80° C. When both phase A and phase B are at temperature, add phase B to phase A with homogenization until batch appears uniform. Continue homogenization for 2 minutes while adding phase C. Remove heat and switch to sweep agitation when batch becomes too thick for homogenizer. Add phase D at 35–40° C. Make up for lost water and stir until room temperature.

Composition H provides excellent, water-resistant SPF protection with a smooth, non-oily and non-greasy skin feel after application.

While the invention has been described with particular reference to certain embodiments thereof, it will be understood that changes and modifications may be made which are within the skill of the art.

Accordingly, it is intended to be bound only by the following claims, in which:

1. A flake composition which will form a bilayer lamellar gel network when placed in an oil-in-water system consisting essentially of (a) a cationic swellant which is a saturated fatty acid selected from stearic or palmitic acid, or mixtures thereof in an adduct of amidopropyldimethyl-2-hydroxyethyl ammonium halide, and (b) a gellant blend of low HLB emulsifiers which includes a saturated fatty alcohol, said gellant blend having a resultant HLB of about 1.5 to 4.5, wherein (a) is made in said saturated fatty alcohol as solvent.

2. A flake composition according to claim 1 wherein said resultant HLB is about 2 to 4.

3. A flake composition according to claim 1 wherein (a) is present therein in a weight % of about 0.5 to 5% and (b) is present therein as the rest of the composition.

4. A flake composition according to claim 3 wherein (a) is 0.75 to 3%.

5. A flake composition according to claim 3 wherein (a) is 1 to 2.

6. A flake composition according to claim 1 wherein (b) is a group of emulsifiers selected from the group consisting of fatty alcohols and esters, and a saturated fatty acid.

7. A flake composition according to claim 6 wherein said fatty alcohol is behenyl alcohol and said fatty ester is glycerol stearate or sorbitan monostearate or mixtures thereof.

8. A flake composition according to claim 6 wherein the weight ratio of fatty ester to fatty alcohol is about 2:1 to about 1.6:1.

9. A flake composition according to claims 6 wherein the weight ratio of fatty acid emulsifier to (a) is about 2:1 to about 4:1.

10. A flake composition according to claim 1 wherein (b) is, by weight, about 30–60% glycerol stearate, about 25–50% cetyl alcohol, about 3–8% behenyl alcohol and about 2–8% of a mixture of palmitic and stearic acids.

11. A personal care formulation which is an oil-in-water system including, by weight, about 2–8% of the composition of claim 1.

12. A personal care formulation according to claim 11 which is a skin care formulation.

13. A personal care formulation according to claim 11 which is a hair conditioning formulation.

14. A personal care formulation according to claim 11 which is a sunscreen formulation.

* * * * *